United States Patent [19]

Heuscher

[11] Patent Number: 5,544,212
[45] Date of Patent: Aug. 6, 1996

[54] SPIRAL CT USING AN INTEGRATING INTERPOLATOR

[75] Inventor: Dominic J. Heuscher, Aurora, Ohio

[73] Assignee: Picker International, Inc., Highland Heights, Ohio

[21] Appl. No.: 344,896

[22] Filed: Nov. 25, 1994

Related U.S. Application Data

[63] Continuation-in-part of Ser. No. 139,318, Oct. 19, 1993, Pat. No. 5,396,418, which is a continuation-in-part of Ser. No. 943,411, Sep. 9, 1992, abandoned, which is a continuation-in-part of Ser. No. 567,300, Aug. 14, 1990, Pat. No. 5,262,946, which is a continuation-in-part of Ser. No. 260,403, Oct. 20, 1988, Pat. No. 4,965,726, and a continuation-in-part of Ser. No. 438,687, Nov. 17, 1989, Pat. No. 5,276,614.

[51] Int. Cl.$^6$ .......................................... A61B 6/03
[52] U.S. Cl. ..................... 378/15; 378/901; 364/413.18
[58] Field of Search .................................. 378/4, 15, 901; 364/413.14, 413.17, 413.18

[56] References Cited

U.S. PATENT DOCUMENTS

| | | | |
|---|---|---|---|
| 5,291,402 | 3/1994 | Pfoh | 364/413.14 |
| 5,345,381 | 9/1994 | Wallschlaeger | 364/413.14 |
| 5,377,250 | 12/1994 | Hu | 378/15 |
| 5,446,799 | 8/1995 | Tuy | 382/132 |
| 5,485,493 | 1/1996 | Heuscher et al. | 378/15 |

OTHER PUBLICATIONS

"Nonlinear Partial Volume Artifacts in X–Ray Computed Tomography" Glover, et al. Med. Phys 7(3), May/Jun. 1980.
"New Algorithm For Reducing Partial Volume Artifacts in Helical CT", Toki, et al., Poster No. 370, Meeting of the Radiological Society of North America, Nov. 29, 1993.
"CT System Made for Versatility", G. E. Medical Systems, Medical Electronics & Equipment News, p. 47, vol. 34, No. 1, Jan./Feb. 1994.

*Primary Examiner*—David P. Porta
*Assistant Examiner*—David Vernon Bruce
*Attorney, Agent, or Firm*—Fay, Sharpe, Beall, Fagan, Minnich & McKee

[57] ABSTRACT

An x-ray source (12) is mounted to a rotatable gantry (16). The x-ray source irradiates an examination region (14) with penetrating radiation as (i) the x-ray source rotates around the examination region and (ii) a patient coach (30) moves a patient axially through the examination region. Detectors (24) positioned on an opposite side of the examination region converts radiation which has traversed the examination region along spiral paths (80). Data from the detectors are collected and stored (40) in spiral data sets. In the prior art spiral data on either side of a thin slice central plane was interpolated into a thin slice data set, each thin slice data set was reconstructed into a thin slice image, and several thin slice images were combined to make a thick slice image with significant partial volume artifacts. By distinction, an integrating interpolator (42) weights (88) data values in several spiral sets in accordance with a weighting values $W_1$, $W_2$, . . . and the weighted sets are combined (90) to form a thick slice data set. The thick slice data set is reconstructed (50) into a thick slice image having reduced partial volume artifacts.

17 Claims, 2 Drawing Sheets

SPIRAL CT USING AN INTEGRATING INTERPOLATOR

This application is a continuation-in-part of U.S. application Ser. No. 08/139,318, filed Oct. 19, 1993, now U.S. Pat. No. 5,396,418, which, in turn, is a continuation-in-part of U.S. application Ser. No. 07/943,411, filed Sep. 9, 1992, now abandoned, which application is a continuation-in-part of U.S. application Ser. No. 07/567,300, filed Aug. 14, 1990, now U.S. Pat. No. 5,262,946, which is a continuation-in-part of U.S. application Ser. No. 07/260,403, filed Oct. 20, 1988, now U.S. Pat. No. 4,965,726 and U.S. application Ser. No. 07/438,687, filed Nov. 17, 1989, now U.S. Pat. No. 5,276,614.

BACKGROUND OF THE INVENTION

The present invention relates to the art of diagnostic imaging. It finds particular application in connection with spiral volume imaging using CT scanners and will be described with particular reference thereto. It is to be appreciated that the present invention will also find application in connection with other types of volume imaging of human patients for medical diagnostic purposes or manufactured articles to detect internal structures or flaws and the like.

In conventional spiral or helical scanning, an x-ray source or tube emits a fan beam of radiation as it rotates continuously around an examination area as a subject support table moves therethrough at a constant, linear velocity. Detectors positioned across the examination region from the x-ray tube convert x-rays which traverse the subject patient into corresponding electronic data. The collected data effectively represents a helical path of constant pitch through the subject or patient. The helical data is reconstructed into a volumetric image representation, typically a series of consecutive thin slice images of the patient.

One technique for reconstructing image slices from the stored spiral data involves interpolating collected spiral data into planar data. For example, for each plane transverse to a central axis, corresponding rays in the two closest spirals to either side of the plane are interpolated to generate one of the rays of the planar data set. This same interpolating procedure is repeated for each ray of a complete data set, e.g. a data set extending over 180°. The data from the transverse plane is reconstructed into a planar or thin slice image representation of the volume image representation using conventional reconstruction techniques.

Heretofore, partial volume artifacts have degraded CT scanner image quality. Prior art techniques have attempted to reduce the adverse effects caused by partial volume artifacts by combining several of the reconstructed thin slice images. Two or more adjacent thin slice images are combined or summed to form a single thick slice image with reduced partial volume artifact effects.

Combining thin slice images has the benefit of retaining low contrast resolution, but suffers from possible motion artifacts due to the long acquisition time for each summed image as well as the additional reconstruction time to generate the several thin slice images prior to combination.

When six thin slice images are combined to reduce partial volume artifacts in the resulting slice representation, six reconstruction operations are first performed. The length of time to perform six reconstructions and combine the resultant six thin slice images into a partial volume artifact reduced thicker slice image causes a significant delay.

The present application contemplates a new and improved scanning technique which overcomes the above referenced problems and others.

SUMMARY OF THE INVENTION

In accordance with of the present invention, a new and improved spiral CT scanner is provided. An x-ray source irradiates an examination region with penetrating radiation as it rotates around the examination region. A patient support moves a patient through the examination region concurrently with rotation of the radiation source. Radiation detectors for converting the received radiation into electronic data. An integrating interpolator combines a selected number of spiral data sets prior to reconstruction into a thick slice image.

One advantage of the present invention is that integration of the electronic data occurs prior to reconstruction of the resulting image. Reducing the number of reconstructions reduces processing time.

Another advantage of the present invention is that partial voluming is selectively reducible.

Another advantage of the present invention is that only selected cross-sectional images of the patient are reconstructed for viewing eliminating unnecessary storage and processing.

Another advantage is that thin slice 3D images can be reconstructed from the same data set.

Yet another advantage resides in the ability to select slice profiles including rectangular profiles.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are for only purposes of illustrating a preferred embodiment and are not to be construed as limiting the invention.

DETAILED DESCRIPTION OF THE PREFERRED EMBODIMENTS

Figure 1:
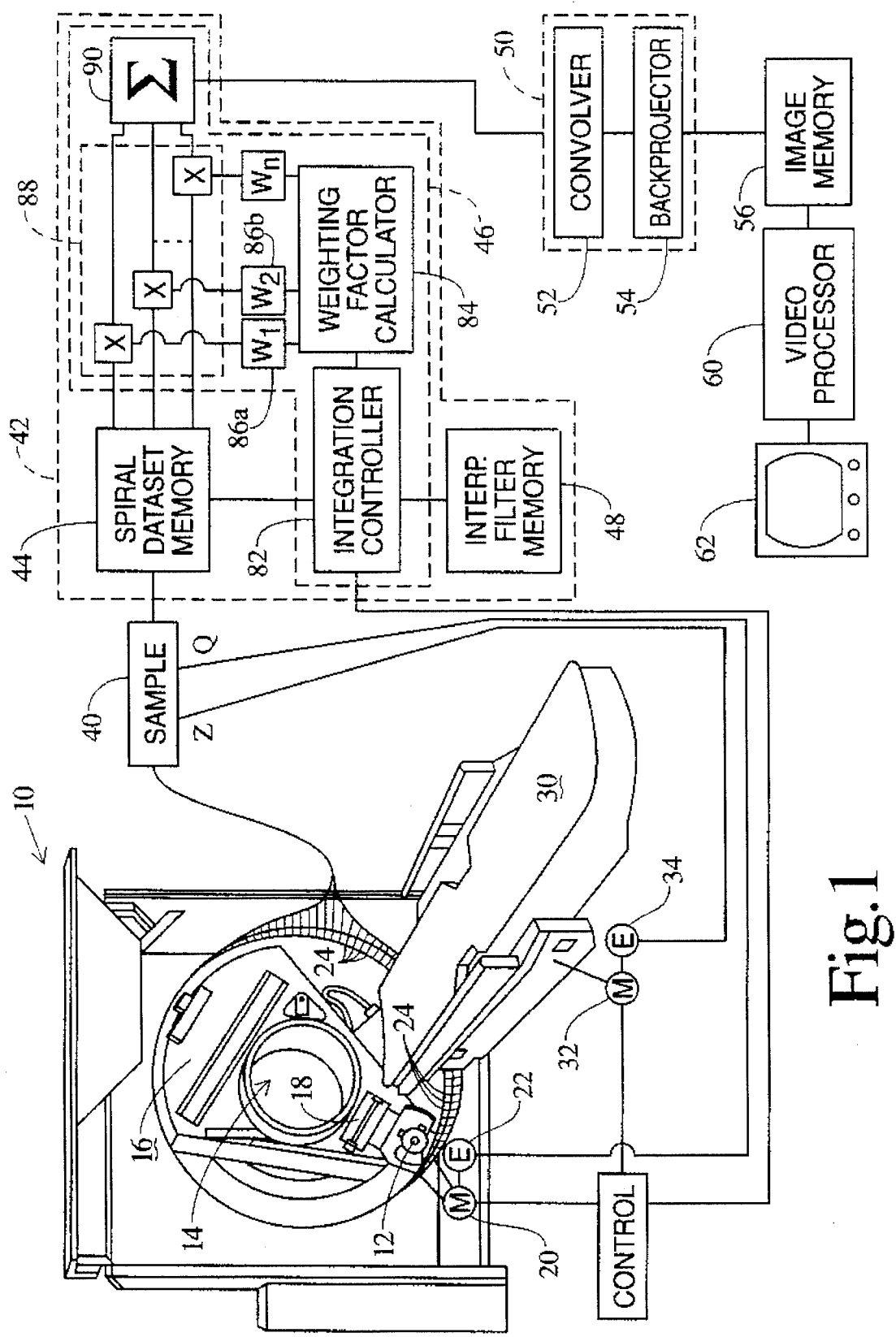
FIG. 1 is a diagrammatic illustration of a spiral CT scanner in accordance with the present invention.

With reference to FIG. 1, a CT scanner 10 includes a radiation source 12, such as an x-ray tube, for projecting a fan beam of radiation through an examination region or scan circle 14. The x-ray source 12 is mounted on a rotatable gantry 16 to rotate the fan beam of radiation around the examination region 14. A collimator and shutter assembly 18 collimates the radiation to a one or more narrow planar beams and selectively gates the beams on and off. The beams may also be gated on and off electronically at the x-ray source. A motor 20 provides motive power for rotating the gantry 16 continuously around the examination region 14. A rotational position encoder 22 is connected with the motor and the gantry to measure the rotational position of the gantry. In the illustrated fourth generation CT scanner, a ring of radiation detectors 24 are mounted peripherally around the examination region.

In a source fan geometry, an arc of detectors which span the radiation emanating from the source are sampled concurrently at short time intervals as the radiation source 12 rotates around the examination region to generate a source fan view. In a detector fan geometry, each detector is sampled a multiplicity of times as the radiation source rotates behind the examination region to generate a detector fan view. The path between the x-ray source and each of the detectors is denoted as a ray. Contiguous fan views which span 180° plus the angle of the fan constitute a complete set of data for reconstruction into a slice image.

A patient support 30 supports a patient subject in a reclined position. A motor 32 advances the patient support through the examination region at a selected, preferably constant velocity. An encoder 34 is connected with the motor 32, the movable patient support 30, and the drive mechanism therebetween for monitoring an axial or longitudinal position of the patient support as it moves the patient through the examination region 14.

A sampling precessor 40 samples the fan views corresponding to each angular position around the examination region 14 for each of a multiplicity of spirals. The apexes of the fan views are disposed along a helix and are defined by an angular orientation $\phi$ around the imaged volume and as longitudinal position along the imaged volume. Data within each fan is further identified by the angle $\alpha$ within the fan.

A view processor 42 converts the spiral sampled views into planar data sets. The view processor includes memory 44 which stores the spiral sampled views. An integrating interpolator 46 integrates corresponding rays of a preselected number of contiguous sets of spiral data with a filter or interpolation function retrieved from a memory 48. The memory 48 stores a plurality of filter or interpolation functions for integrating different numbers of spiral fan views. The more views that are combined, the thicker the corresponding slice.

Thereafter, the combined set of data is conveyed to a reconstruction processor 50. The reconstruction processor of the preferred embodiment includes a convolver 52 which convolves the thick slice interpolated data sets and a backprojector 54. The backprojector 54 back projects the convolved data sets into a reconstructed image memory 56. A video processor 60 retrieves slice, projection, 3D rendering, and other image information from the image memory 56 and formats the image data into appropriate formats for display on video monitor 62 or the like.

Figure 2:
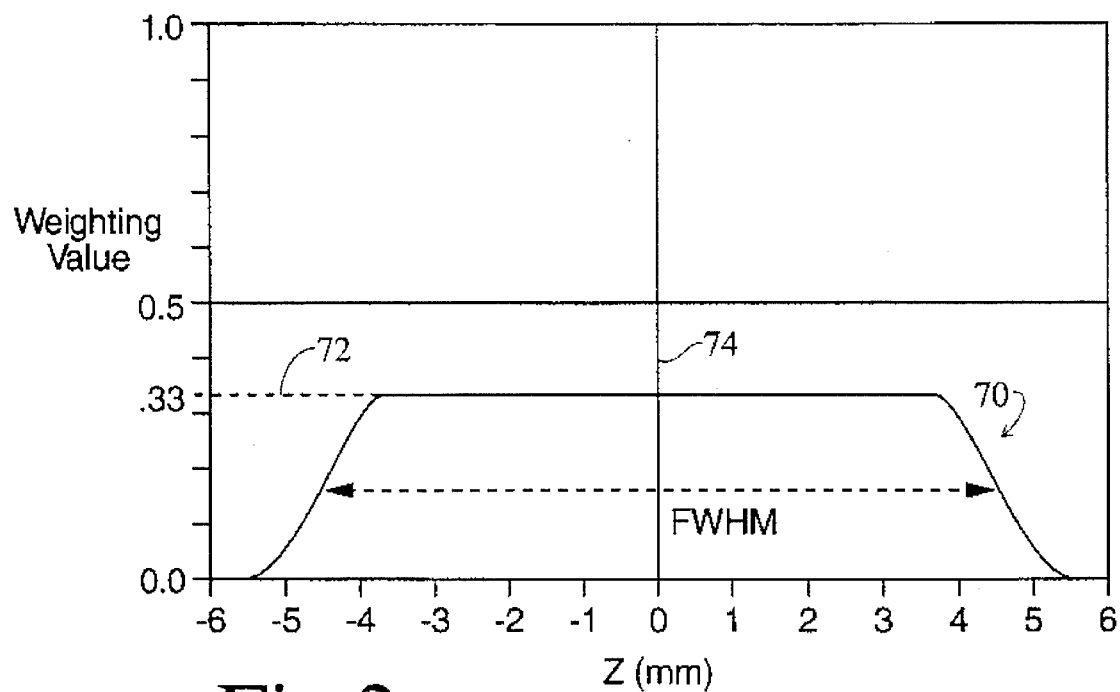
FIG. 2 illustrates the interpolation function with an integration factor equal to 3.

With reference to FIG. 2, an interpolation function 70 is a linear weighting function whose values are dependent upon the number of sets or views selected for combination to form a thick slice image of the subject patient. The interpolation function is defined especially over two or more revolutions of the x-ray source 12. As shown in FIG. 2, the interpolator function has a flat plateau and tapers at each end over a distance comparable to a rotation angle of ½ of a revolution angle. The interpolator function is normalized such that the area under the curve is substantially unity. In other words, the plateaus value of the interpolator is inversely proportional to the width of the thick slice. The interpolator function of FIG. 2 has a maximum weighting value 72 of 0.33 which is inversely proportional to a selected three rotations sought to be combined, i.e. the integration factor. Using this interpolation function, the reconstructed images have an effective slice thickness to the distance traveled in 3 revolutions of the x-ray source.

Figure 3:
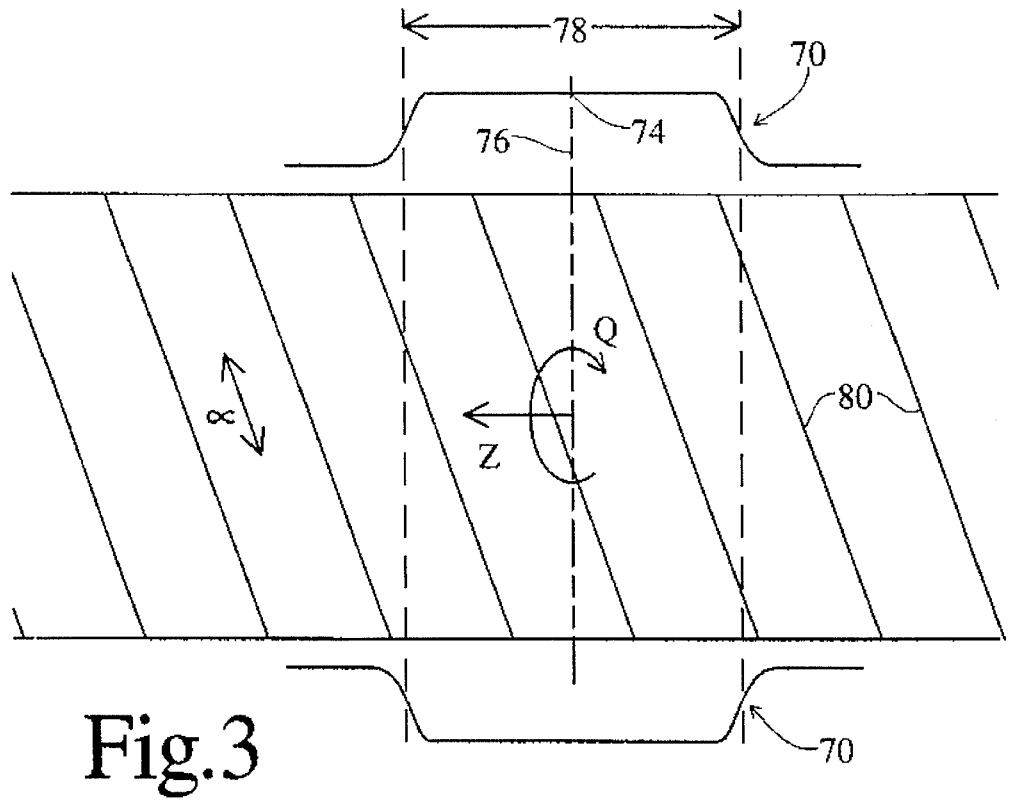
FIG. 3 is a diagrammatic of the geometric relationships of spiral data, transverse slices, and the interpolation function.

With reference to FIGS. 2 and 3, a center point 74 of the filter function is fixed to match a center 76 of a thick slice 78. It will be appreciated that the data follows a helical path while the center of the filter is axially fixed. Thus, when the next corresponding rays of each of the adjoining data sets are integrated, their intersection points with the filter shifts and the filter factors normally change. Depending on the pitch, one data set may spiral out of the filter as another spirals in. The data fans along spiral paths 80 are arranged into 180° plus fan angle data sets which the "plus fan angle" fans being duplicative with adjacent data sets. Accordingly, the data sets are each nominally one-half the distance traveled by the patient in time that the x-ray source rotates one revolution. Of course, the data sets can span 360°, can have non-duplicative "plus fan angle" fan views in which case the data sets are nominally spaced apart by the distance that the patient travels in the time the x-ray source rotates one revolution. Changing the pitch of the helix changes the physical spacing of the data sets.

An integration controller 82 converts the physical dimension of the selected thick slice into data space, e.g. average number of spanned spiral data sets. Each data set value that is encountered within the plateau at the top of the filter curve, between about 3¾ mm and −3¾ mm of the center of the thick slice, is multiplied by 0.33 in the example of FIG. 2. Data set values in data space regions between +3¾ and +5½ and between −3¾ and −5½ are multiplied by the corresponding smaller fraction. The integration controller 82 controls a filter or weighting factor calculator 84 which calculates the 0 to 0.33 or other appropriate weighting values $W_1, W_2, \ldots W_n$ for each retrieved data value. The filter factors are loaded in filter factor buffers 86a, 86b . . . A multiplier 88 multiplies each of the received data set values by the corresponding filter function. A summing amplifier 90 sums all weighted data values corresponding to rays spaced 360° apart. The resulting 260° weighted and summed data set is then convolved and backprojected by the processor 50.

In the illustrated embodiment, to obtain equivalent thick slice thickness of about 10 mm with a 3 mm spiral scan width an integration factor of 3 would be used with a scan pitch of 1.0 to 1.25. Larger pitch factors will result in unnecessarily broad slice profiles. Using this interpolator, the measured slice thickness corresponds to the following formula:

Measured Slice Thickness (FWHM) =(Pitch Factor)x(Integration Factor)x(Slice Thickness)

The invention has been described with reference to a preferred embodiment. Obviously modifications and alternations will occur to others upon reading and understanding the preceding detailed description. It is intended that the invention be construed as including all such modifications and alterations insofar as they come within the scope of the independent claims or the equivalence thereof.

Having thus described the preferred embodiments, the invention is claimed to be:

1. In a CT scanner which includes an x-ray source for irradiating an examination region with penetrating radiation, the x-ray source being mounted for rotation around the examination region, a patient support which moves a patient through the examination region concurrently with rotation of the x-ray source, radiation detectors disposed across the examination region from the x-ray source to receive x-ray radiation which has traversed the examination region and convert the received radiation into electronic data, a data set memory which stores the electronic data in spiral data sets where each spiral data set contains data relating to less than 360° around the patient, the improvement comprising:

an integrating interpolator which combines the electronic data from a predetermined plural number of the spiral data sets in accordance with a filter function into a planar data set; and a reconstruction processor which reconstructs the planar data set into a slice image representation.

2. In the CT scanner as set forth in claim 1, the integration interpolator including:

a filter function memory which stores at least a selected filter function that indicates corresponding weighting factors for each of the spiral data sets;

a multiplier for combining the weighting factors with the spiral data set to generate weighted data; and an adder for combining the weighted data.

3. A tomographic scanner comprising:

an x-ray source for irradiating an examination region with a fan beam of penetrating radiation, the x-ray source being mounted for rotation about the examination region;

a subject support for supporting a subject such that the examination region and the subject undergo relative movement along an axis of movement concurrently with rotation of the x-ray source around the axis of movement;

radiation detectors disposed across the examination region from the x-ray source for receiving rays of the fan beam which traverse the examination region and converting the received rays into electronic data;

a memory for storing spiral slice sets of the electronic data, each set consisting of electronic data representing a slice through the subject along a spiral path segment during at least a half rotation of the x-ray source;

an integrating interpolator for weighting and integrating a plurality of spiral slice data sets to generate a thick slice data set representing a slice through the subject which (1) is in a plane transverse to the direction of movement and (2) is as thick as a plurality of spiral slices; and a reconstruction processor for reconstructing the thick slice data sets into thick slice image representations for storage in an image memory.

4. The CT scanner as set forth in claim 3 further including a video processor for converting image data from the image memory into a thick slice cross sectional image for display on a monitor.

5. The tomographic scanner as set forth in claim 3 wherein the integrating interpolator includes:

a weighting means for (1) weighting data from the spiral slice data sets within a preselected number of spiral slice thicknesses of a central plane of the thick slice with a first weighting value selected in accordance with the preselected number and (2) weighting data from the spiral slice data sets beyond the preselected number of spiral slice thicknesses of the thick slice central plane with a roll-off filter that diminishes from the first weighting value to zero with distance from the thick slice central plane; and a means for combining the weighted and roll-off filtered spiral slice data into the thick slice data set.

6. The tomographic scanner of claim 5 wherein the weighting values are less than 1.

7. A tomographic scanner comprising:

an radiation source for irradiating an examination region with penetrating radiation from a multiplicity of directions;

a patient support for moving a patient and the examination region axially relative to each other such that the radiation source spirals around the patient;

radiation detectors disposed across the examination region for receiving radiation which has traversed the examination region and for converting the received radiation into spiral slice electronic data;

an interpolator for interpolating the spiral slice data into planar slice data sets representing a series of parallel slices;

an integrator for combining a plurality of the data sets into a combined data set; and reconstruction processor for reconstructing the combined data set into a slice image representation.

8. The tomographic scanner of claim 7 wherein the interpolator includes a means for weighting electronic data of the selected planar slice data sets with weighting values.

9. The tomographic scanner of claim 8 wherein the interpolator further includes a means for generating the weighting values as a function of position along a longitudinal axis of the patient.

10. The tomographic scanner of claim 9 wherein the weighting value generating means generates weighting values inversely proportional to a number of planar slice sets combined.

11. A tomographic scanner comprising:

a radiation source for irradiating an examination region with a fan beam of penetrating radiation, the fan beam being collimated to a collimated beam thickness, the radiation source being mounted to rotate the fan beam about the examination region;

a subject support for supporting a subject such that the examination region and the subject undergo relative movement along an axis of movement concurrently with rotation of the radiation fan beam around the axis of movement;

radiation detectors disposed across the examination region from the radiation fan beam for receiving rays of the fan beam which traverse the examination region and converting the received rays into electronic data;

a memory for storing the electronic data, the stored electronic data being collected over a plurality of fan beam rotations and representing radiation passing along a multiplicity of rays through the subject along a spiral path;

an integrating interpolator for weighting and integrating a plurality of subsets of the stored electronic data to generate slice data sets representing selected slices through the subject, each slice data set including a portion of the electronic data spanning at least a half rotation of the fan beam which slice data sets (1) are in a plane transverse to the direction of axial movement and (2) are collected over an axial distance greater than the collimated beam thickness; and a reconstruction processor for reconstructing the slice data sets into slice image representations representing slices that are thicker than the collimated beam thickness.

12. A tomographic scanner comprising:

a radiation source for irradiating an examination region with penetrating radiation from a multiplicity of directions;

a patient support for moving a patient and the examination region axially relative to each other such that the radiation source spirals around the patient;

radiation detectors disposed across the examination region for receiving radiation which has traversed the examination region and for converting the received radiation into spiral electronic data;

a processor for interpolating and integrating the spiral electronic data into data sets representing a series of parallel slices; and a reconstruction processor for reconstructing the data sets into slice image representations.

13. A method generating a cross-sectional image of a patient comprising:

irradiating the examination region with penetrating radiation from a penetrating radiation source;

rotating the radiation source around the examination region;

moving a patient through the examination region as the radiation source rotates around the examination region;

detecting radiation which has traversed the examination region and converting the detected irradiation into electronic data;

storing the electronic data;

weighting selected subsets of the electronic data, the weighting being inversely proportional to a number of the selected subsets;

combining the weighted electronic data subsets; and, reconstructing the combined electronic data subsets into an electronic image representation.

14. A method of reducing partial image artifacts from cross-sectional images, the method comprising:

irradiating a patient with a beam of radiation collimated to a collimation thickness and moving the beam and patient to irradiate the patient along a spiral path;

detecting radiation which has traversed the examination region;

converting the detected radiation into electronic data representing a plurality of revolutions along the spiral path;

storing the electronic data;

selecting a slice thickness thicker than the collimation thickness;

generating weighting values in accordance with the selected slice thickness;

weighting subsets of the electronic data in accordance with corresponding weighting values;

combining the weighted selected electronic data subsets;

reconstructed the combined weighted electronic data subsets into a slice image representation, whereby the slice image representation depicts a slice which is selectively electronically broadened relative to the collimation thickness.

15. The method of claim 14 wherein the weighting values for electronic data subsets adjacent a central transverse plane of the slice are inversely proportional to the number of subsets selected for combination.

16. The method as set forth in claim 15 wherein the weighting values decrease with distance from the central transverse plane.

17. In a CT scanner which includes a radiation source for irradiating an examination region with penetrating radiation, the radiation source being mounted for continuous rotation around the examination region, a patient support which moves a patient through the examination region concurrently with rotation of the radiation source, radiation detectors disposed across the examination region from the radiation source to receive radiation which has traversed the examination region and convert the received radiation into a spiral data set of electronic data representing a plurality of spirals around the patient, a data memory which stores the spiral data set, the improvement comprising:

an integrating interpolator which combines the electronic data from a selected plural number of subsets of spiral data set with a filter function, each subset containing data relating to less than 360° around the patient; and a reconstruction processor which reconstructs the filtered spiral data subsets into slice image representations.

* * * * *